(12) United States Patent
Lilienfeld-Toal

(10) Patent No.: US 6,484,044 B1
(45) Date of Patent: Nov. 19, 2002

(54) APPARATUS AND METHOD FOR DETECTING A SUBSTANCE

(76) Inventor: Hermann v. Lilienfeld-Toal, Wilhelm-Schöffer-Strasse 33, D-63571 Gelnhausen (DE)

( * ) Notice: Subject to any disclaimer, the term of this patent is extended or adjusted under 35 U.S.C. 154(b) by 0 days.

(21) Appl. No.: 09/560,169

(22) Filed: Apr. 28, 2000

(30) Foreign Application Priority Data

| Apr. 30, 1999 | (DE) | 199 19 814 |
| Aug. 9, 1999 | (DE) | 199 37 528 |

(51) Int. Cl.⁷ ............................................. A61B 5/00
(52) U.S. Cl. .................. 600/316; 600/310; 600/365; 600/322
(58) Field of Search ................. 600/309–310, 600/322–324, 326, 328, 315–316, 365

(56) References Cited

U.S. PATENT DOCUMENTS

| 5,313,941 A | | 5/1994 | Braig et al. | |
| 5,348,002 A | * | 9/1994 | Caro | 600/310 |
| 5,941,821 A | * | 8/1999 | Chou | 600/316 |
| 6,104,942 A | * | 8/2000 | Kruger | 600/407 |
| 6,178,346 B1 | * | 1/2001 | Amundson et al. | 600/473 |

FOREIGN PATENT DOCUMENTS

| DE | 4446390 C1 | 7/1996 | G01N/21/25 |
| EP | 0282234 | 9/1988 | |
| WO | 9118548 | 12/1991 | |

OTHER PUBLICATIONS

B.A. Paldus et al., Photoacoustic Spectroscopy Using Quantum–Cascade Lasers; *Optics Letters*, vol. 24, No. 3 (Feb. 1, 1999); 3 pgs.
"Quantum Cascade Laser," Jerome Faist et al., *Science*, Apr. 22, 1994.
"Glucose determination by a pulsed photoacoustic technique: an experimental study using a gelatin–based tissue phantom," Quan et al., *Phys. Med. Biol.*, 39, 1993, pp. 1911–1922.
"Laser photoacoustic determination of physiological glucose concentrations in human whole blood," *Medical & Biological Engineering & Computing*, May 1993.

* cited by examiner

*Primary Examiner*—Eric F. Winakur
*Assistant Examiner*—Matthew Kremer
(74) *Attorney, Agent, or Firm*—Dorsey & Whitney LLP

(57) ABSTRACT

An apparatus for detecting a substance in a sample, particularly for in vivo detecting and measuring glucose in body tissue or blood contains a semiconductor laser for emitting mid-infrared laser light at at least two discrete wavelengths, each at a different peak or valley in the absorption spectrum of the substance in the sample. A photoacoustic detector detects acoustic signals originating from absorption of the laser light. An indication unit evaluates the acoustic signals separately for each wavelength and calculates a detection result based on all acoustic signals from the different wavelengths.

20 Claims, 5 Drawing Sheets

APPARATUS AND METHOD FOR DETECTING A SUBSTANCE

BACKGROUND OF THE INVENTION

The invention relates to an apparatus and a method for detecting a substance in a sample, particularly for detecting and measuring the concentration of a substance such as glucose in body fluid or tissue.

Insulin dependent diabetics have to monitor their blood glucose concentrations at regular intervals. At present, this is mostly done by taking a blood sample and analyzing it outside the patient's body. Patients who monitor their blood glucose level themselves use a finger lance to obtain a drop of blood which is applied to a reagent strip for analyzing. Naturally this process causes pain and discomfort. There have been various attempts, therefore, to detect blood glucose concentrations in vivo.

EP-A-282234 proposes in vivo detection of glucose in the blood stream by infrared spectroscopy using a laser beam penetrating a person's skin. The wavelength of the laser beam is selected in the near-infrared (NIR) range of 0.76 to 2.5 $\mu$m.

As explained by H. A. Mac Kenzie et al. in Phys. Med. Biol. 38 (1993) 1911–1922 and in Clinical Chemistry 45:9 (1999) 1587–1595, the near-infrared range and in particular the wavelength region of 1 to 2 $\mu$m is preferred for non-invasive blood glucose measurement as the absorption of light of other wavelengths in the human skin is too large for the light to penetrate to a suitable depth for interaction with blood. In Medical & Biological Engineering & Computing, May 1993, 284 to 290, Mac Kenzie et al. report also the use of the mid-infrared (MIR) wavelength region of 2.5 to 25 $\mu$m for glucose measurements. But due to the very low skin transmission at these wavelengths, they have not measured glucose concentrations in vivo. The mid-infrared light source used is a $CO_2$ laser and the glucose concentration is obtained by measuring the absorption coefficient in the sample at a certain wavelength and relating it to the absorption coefficient of distilled water at the same wavelength.

In the above-discussed prior art, the optical absorption coefficient is measured through the photoacoustic effect: optical absorption of infrared radiation leads to molecular resonance such as vibrational modes of C—O bonds in glucose; when de-excitation occurs through nonradiative molecular transitions, the sample is locally heated, producing a temperature gradient and a material strain. The strain can be detected by an acoustic sensor. Localized heating and expansion of the material from a pulse of light produces a pulse of an acoustic wave.

The use of a photoacoustic detector for in vivo measuring blood glucose levels is disclosed in WO 91/18548. In this prior art, infrared light of two wavelengths in the MIR region is applied at two different locations to a person's skin. One wavelength is selected such that blood glucose shows a specific absorption and the other wavelength is selected such that there is no specific absorption by glucose. An acoustic detector detects the pressure difference between the locations where the different wavelengths are applied.

A simple arrangement for measuring blood glucose levels by infrared transmission through a person's finger is disclosed in U.S. Pat. No. 5,313,941. This arrangement uses a filament infrared source and silicon photodetectors with filters to select a certain wavelength band from the source.

None of the above techniques has yet led to a practically usable device for noninvasive detection of glucose. At infrared intensities which are practically usable without unduly heating or even burning a person's skin, all the known techniques are not sensitive and reliable enough or are too bulky for daily use.

SUMMARY

It is an object of the invention to provide a simple and reliable apparatus and method for noninvasive detection of a substance in a sample.

This object is solved by the apparatus and the method set forth in the independent claims. The dependent claims are directed to further embodiments of the invention.

Substances of interest such as glucose have covalent bonds with fundamental resonance frequencies in the mid-infrared region of the light spectrum, i.e. at frequencies corresponding to infrared light wavelengths from 2.5 to 25 $\mu$m (wavenumbers of 4000 to 400 $cm^{-1}$). Hence, the mid-infrared region of the absorption spectrum of these substances contains relatively narrow absorption lines specific to each individual substance. This is an advantage over the use of the near infrared region at wavelengths from 0.76 to 2.5 $\mu$m where infrared absorption by the substances of interest is due to harmonics of the oscillating molecular bonds and absorption bands are broader, overlap each other, have smaller and wider peaks and it is thus more difficult to attribute absorption to the substance to be detected.

What was previously believed a disadvantage of noninvasive detection of substances such as glucose in body fluids or tissue by mid infrared spectroscopy, namely the high parasitic absorption of mid infrared light by water is overcome by detecting absorption through the photoacoustic effect and by using laser light at a plurality of discrete wavelengths.

The use of the photoacoustic effect for detecting infrared light absorption has the advantage of enabling detection of the substance in a noninvasive technique from within a sample even if light absorption by the sample is too high to allow detecting the substance from transmitted or reflected light.

Irradiating the sample with laser light of at least two distinct and discrete wavelengths at a peak or valley in the absorption spectrum of the substance to be detected in the sample has two effects. Firstly, these are the wavelengths where the absorbance is less dependent on wavelength variations and on a possible shift in the absorption lines due to unknown other components in the sample. Secondly, unnecessary heating of the sample by light of other wavelengths such as in conventional spectroscopy with infrared sources emitting a broad range of wavelengths is avoided. The admissible light intensity can therefore be concentrated on the discrete wavelengths which offer the most accurate results.

The features of the present invention improve the accuracy of the detection. A measurement at the same location of the sample in accordance with the present invention avoids errors from sample inhomogeneities.

A preferred laser device includes a semiconductor laser having a quantum well structure. Quantum well structures are made by alternating layers of different semiconductor material and form energy sub-bands wherein sub-band transitions are used for operation of the laser. The transition energy depends on the semiconductor material and on the layer thickness and can be adjusted to meet the wavelength requirements of the invention. One such laser device is the quantum cascade laser. A description of the quantum cascade laser can be found in J. Faist: "Quantum Cascade Laser" Science, 264 (1994) 553 to 556.

The present invention relates to the measurement of the concentration of the detected substance.

An embodiment of the present invention will now be described with reference to the drawings.

DETAILED DESCRIPTION

Figure 1:
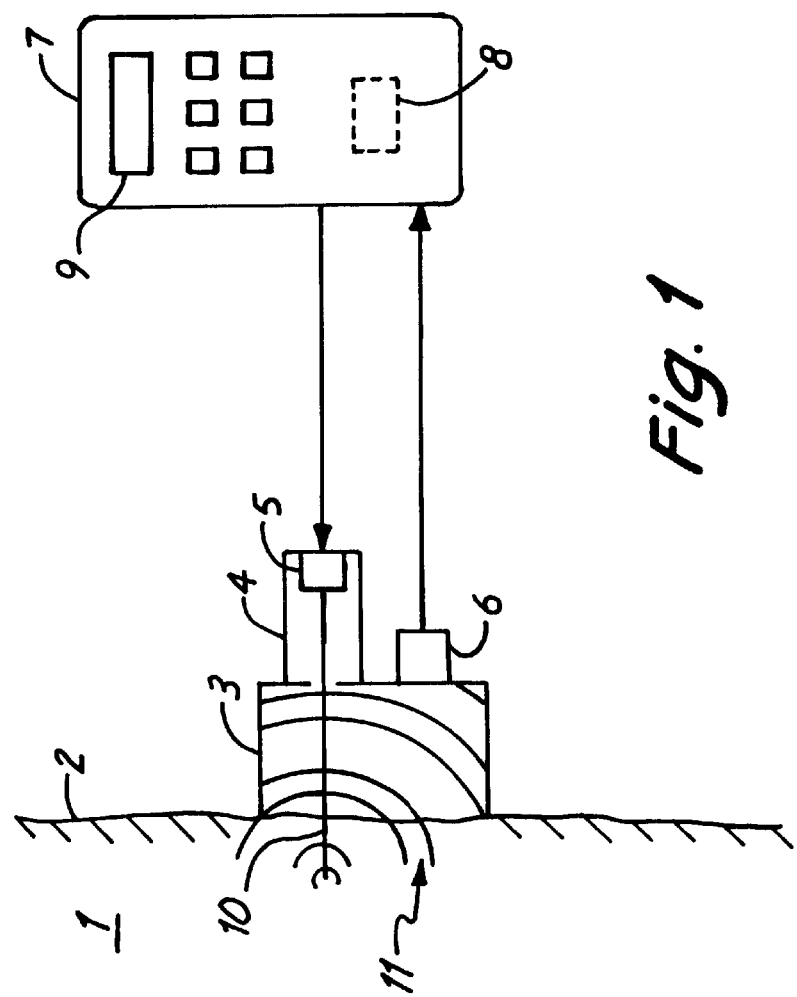
FIG. 1 shows an apparatus for detecting and measuring glucose in vivo in a person's body tissue or blood.

The apparatus shown in FIG. 1 is suitable for detecting and measuring in vivo the glucose concentration in a person's body tissue 1 or blood. It includes a cavity 3 which is placed on a person's skin 2. Attached to the cavity 3 is a laser device 4 including a quantum cascade laser 5. Also attached to the cavity 3 is a piezoelectric transducer 6 acting as a microphone.

The quantum cascade laser 5 and the piezoelectric transducer 6 are connected to a control unit 7 comprising a microcontroller 8 and a display 9.

To detect and measure the glucose concentration in the body tissue 1, the microcontroller 8 in the control unit 7 drives the quantum cascade laser 5 so as to emit pulses of a laser beam 10 which penetrate the skin 2 and enter the body tissue 1. Where the laser beam 10 is absorbed in the body tissue 1, the tissue is locally heated. The thermal expansion resulting from the localised heating initiates an acoustic pulse and the pulsed laser beam 10 thus leads to a pulse train of acoustic signals 11 which originates in the region where the laser beam 10 is absorbed. The pulse train 11 propagates into the cavity 3 and is detected by the piezoelectric transducer 6. Preferably, the pulse frequency of the laser beam 10 is selected by the controller 8 so as to meet the acoustic resonance frequency of the cavity 3 which thus amplifies the acoustic pulses 11.

The microcontroller 8 determines the peak-to-peak amplitude of each acoustic pulse 11 detected by the piezoelectric transducer 6. The peak-to-peak amplitude is a measure of the absorbed energy of the laser beam pulse in the body tissue 1. Preferably, the microcontroller 8 discards a portion of each acoustic pulse which, in accordance with the traveling time of the pulse, originates from a portion of the body tissue 1 where no useful information on the glucose concentration is expected. For example, to disregard acoustic signals originating from absorption of the laser beam in the outer layers of the skin 2, the first part of each acoustic pulse is discarded and the peak-to-peak amplitude is obtained from later portions of the pulse.

The wavelength of the MIR laser light beam 10 is one where the absorbed energy depends on the glucose concentration in the body tissue 1. Moreover, the voltages and currents applied to the quantum cascade laser 5 are changed after a predetermined number of laser beam pulses so as to tune the laser 5 to a different wavelength where the absorbance depends again on the glucose concentration. In this manner, at least three different wavelengths in the mid-infrared range are sequentially scanned. The selected wavelengths are at peaks and valleys, i.e. at relative maxima and minima of the absorption spectrum of glucose in body tissue, blood or water.

Figure 2:
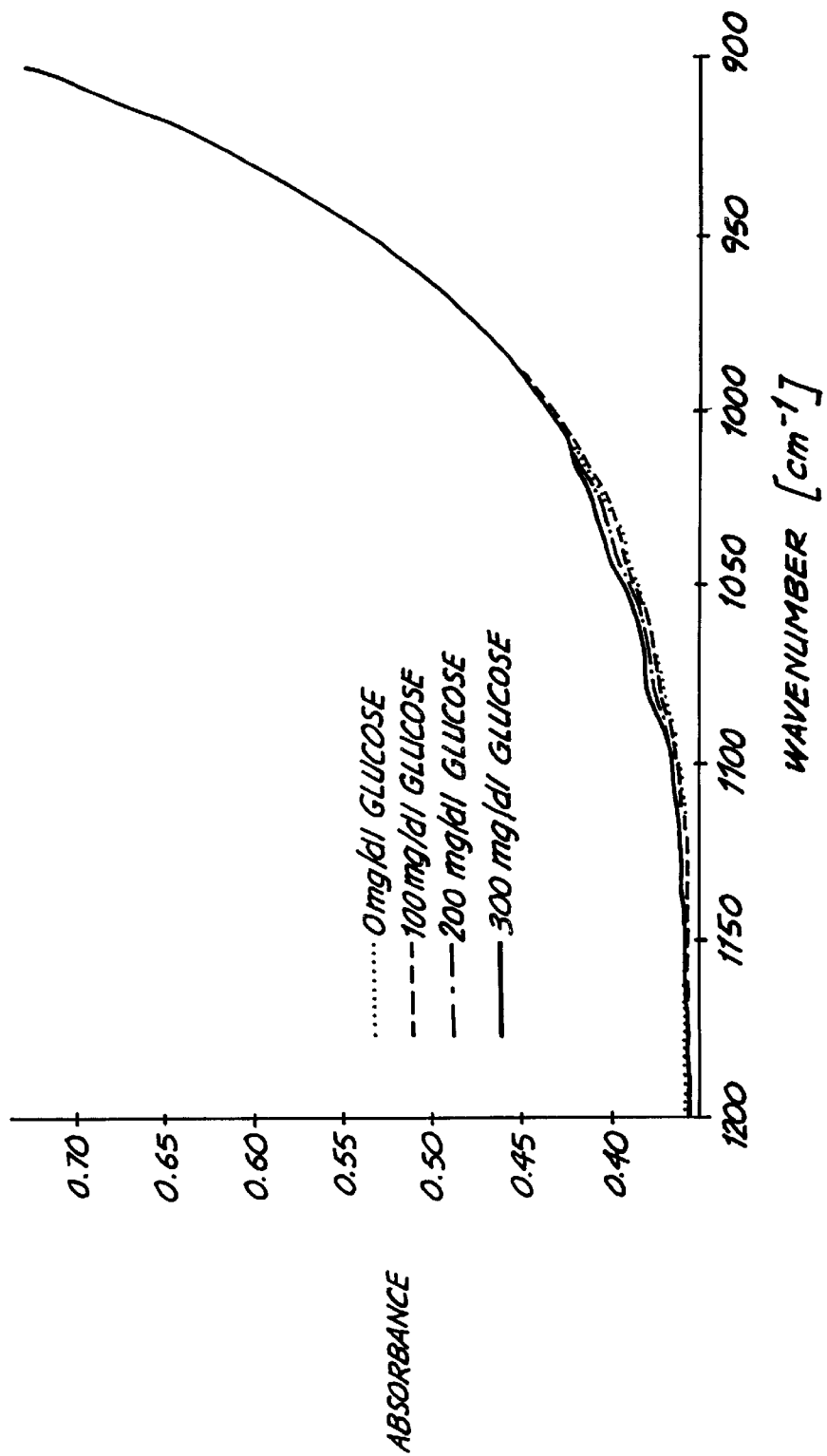
FIG. 2 shows absorption spectra of aqueous glucose solutions of different concentrations, and an absorption spectrum of distilled water.
Figure 3:
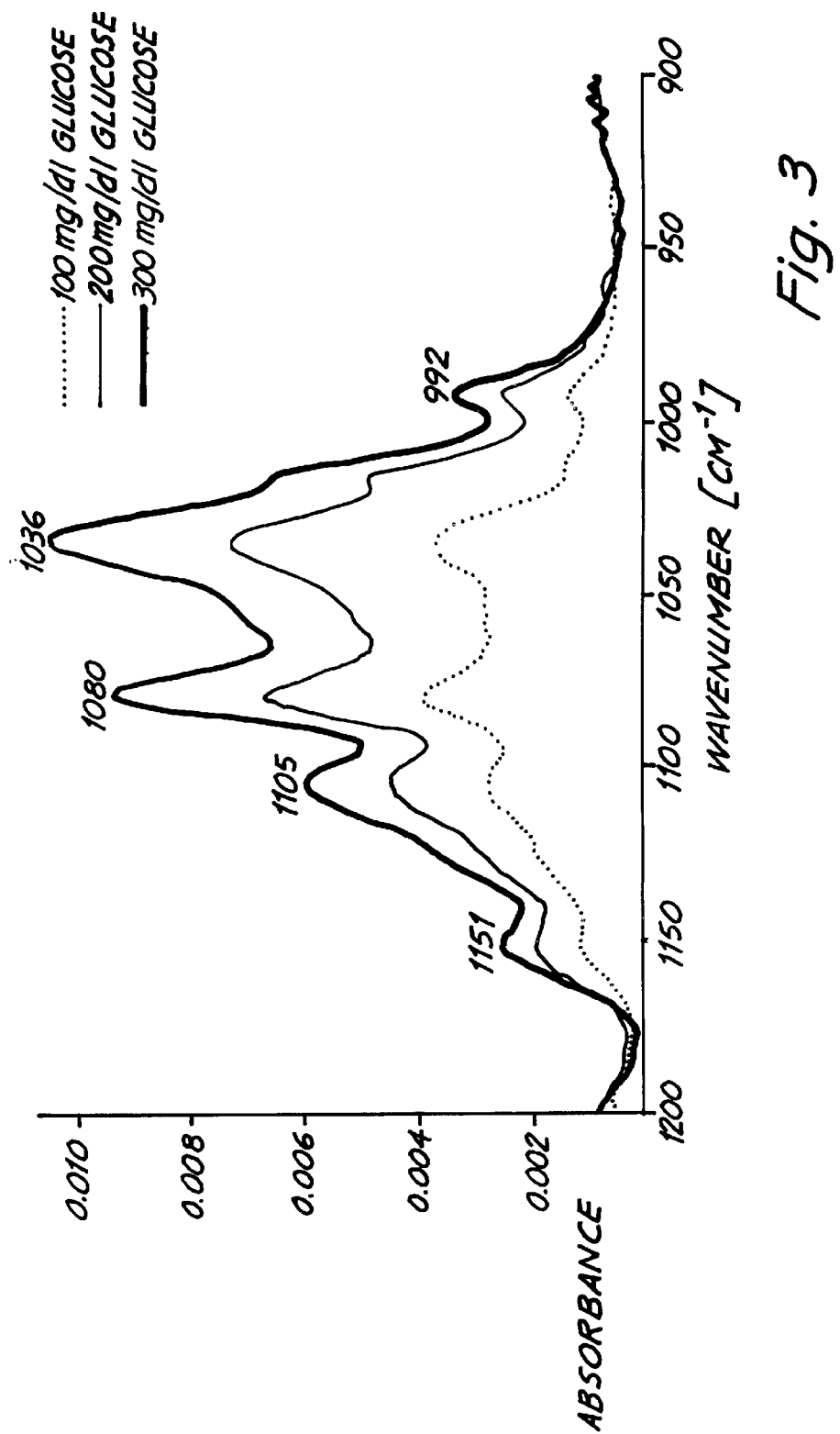
FIG. 3 shows the glucose solution spectra of FIG. 2 with the spectrum of distilled water subtracted.

FIG. 2 shows absorption spectra of aqueous glucose solutions with 100, 200 and 300 mg glucose per dl water (i.e. per 0.1 l water). Also shown is the absorption spectrum of distilled water (0 mg/dl glucose). FIG. 3 shows each spectrum of the glucose concentrations with the spectrum of distilled water subtracted. Thus, the spectra shown in FIG. 3 are those of glucose alone in a water environment. As can be seen from FIG. 3, absorption maxima occur at wavenumbers of 1151, 1105, 1080, 1036 and 992 $cm^{-1}$ for example. And absorption minima occur at wavenumbers of 1181, 1140, 1094, 1066 and 1014 $cm^{-1}$. Preferably, the quantum cascade laser 5 is tuned to scan through all these wavenumbers one after the other with a number of pulses for each wavenumber. If the laser used cannot be tuned over this range, the laser device 4 of this embodiment could be modified to include a plurality of lasers each for a specific wavelength or wavelength range, preferably on the same monolithic device.

The microcontroller 8 calculates the glucose concentration by a least square calculation referring to reference spectra such as shown in FIGS. 2 or 3 for known glucose concentrations. The calculated concentration is displayed on display 9. Alternatively, the glucose concentration could also be calculated from an average of concentrations obtained from the absorptions at each wavelength relative to a reference absorption for a reference glucose concentration determined beforehand.

Preferably, the microcontroller 8 calculates also the error of the least square calculation, i.e. the root of mean square error and makes a selection of only portions of each acoustic pulse and a selection of those acoustic pulses which originate from laser beam pulses of selected wavelengths so as to minimise the error. The selection can be chosen by trial and error among a number of pre-prepared selections until the error is smaller than a certain value. Thereby, the measurement of the glucose concentration focuses on an area within the tissue 1 where the measurement is most reliable, for example a blood vessel.

The measurement principle of the present embodiment has been tested in the measurement of glucose concentrations in milk. Milk has been used as a testing solution instead of blood because it is readily available and resembles blood in that a number of substances are present which could potentially disturb the measurement. These substances are e.g. lactose, proteins and fat.

Figure 4:
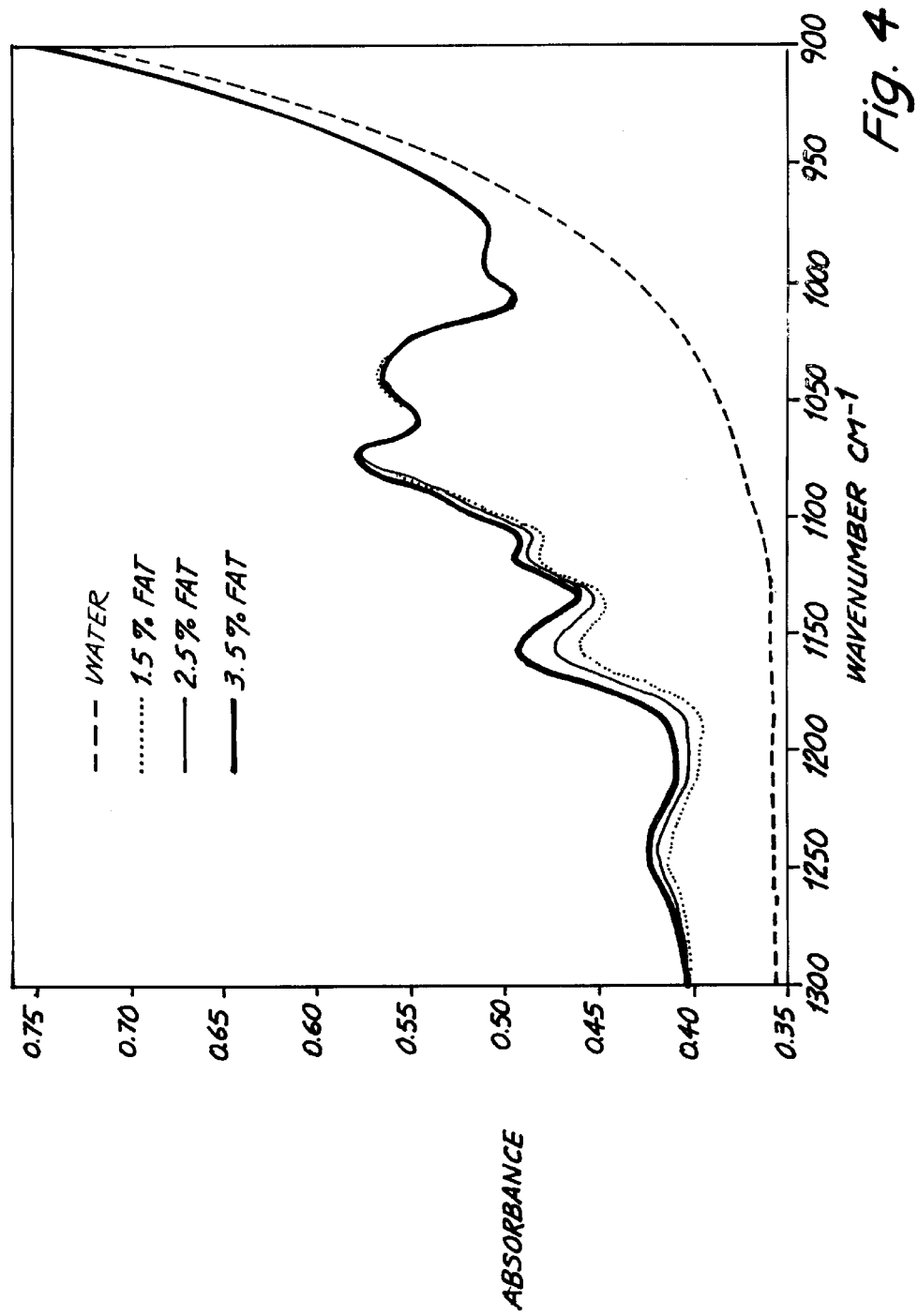
FIG. 4 shows absorption spectra of milk with glucose and with fat in various concentrations, and an absorption spectrum of distilled water.
Figure 5:
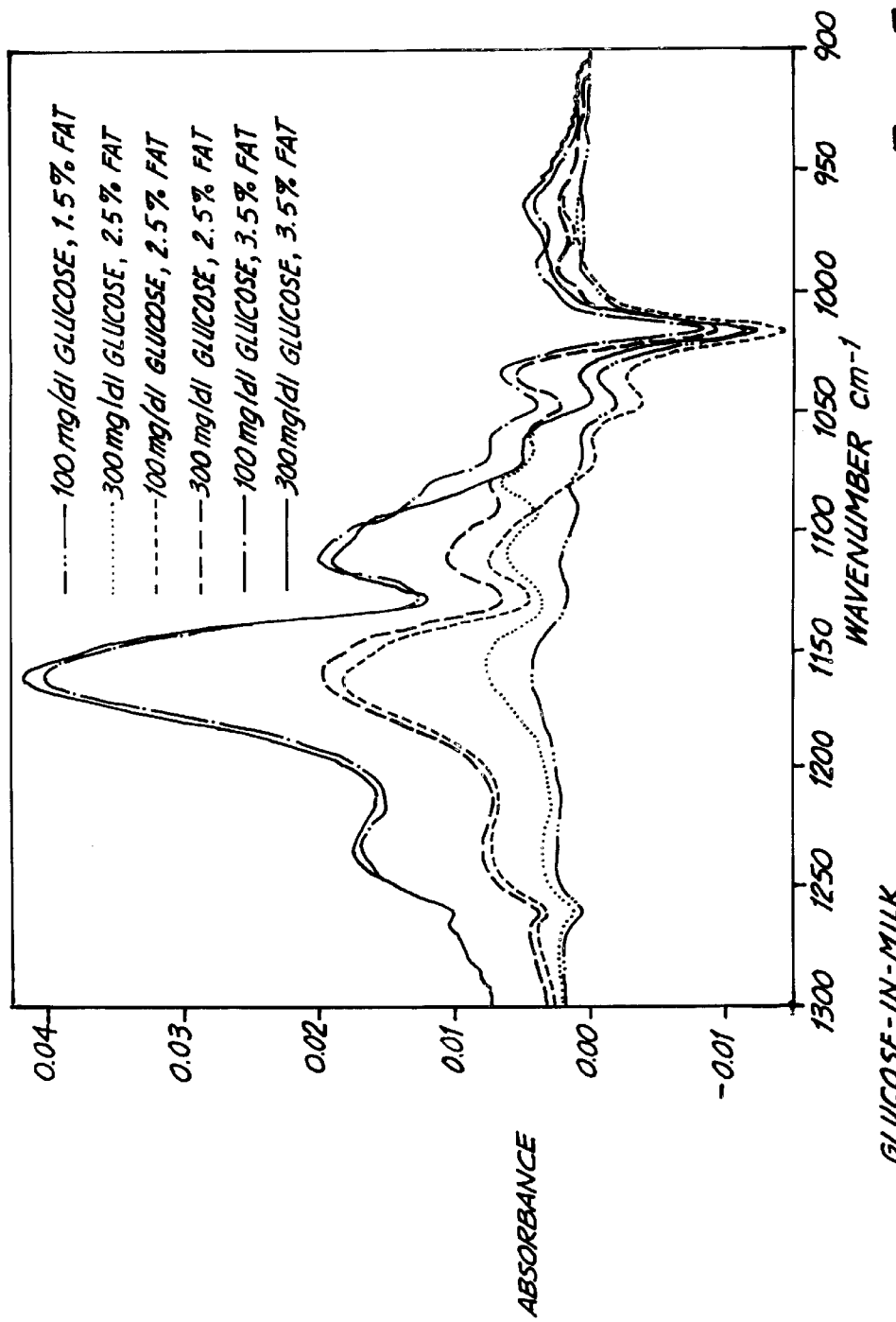
FIG. 5 shows absorption spectra of milk with glucose and fat in different concentrations with the absorption spectrum of milk without glucose subtracted.

The absorption spectra of milk with 100 mg glucose per dl but different amounts of fat, namely 1.5, 2.5 and 3.5 percent fat are shown in FIG. 4 together with the absorption spectrum of distilled water. FIG. 5 shows absorption spectra of solutions with different glucose concentrations in milk of different fat concentrations, after a spectrum of a solution with 0 mg glucose per dl and 1.5 percent fat has been subtracted from each of them. The spectra have been obtained with a spectrometer made by Bruker.

The glucose concentration in an unknown solution can be obtained from spectra of known glucose concentrations (such as FIGS. 4 and 5) by measuring absorbance values and by a partial least square fit (PLS). The PLS fit is based on an algorithm by Carl-Friedrich Gauss: A standard curve based on spectra of known concentrations is calculated such that the sum of the squared differences between the measured values of the unknown solution and the corresponding values in the standard curve is minimized. The concentration is derived from the thus calculated standard curve.

The spectra of FIGS. 4 and 5 include absorption bands useful for glucose concentration measurements in the wavenumber region from 1181 to 960 cm$^{-1}$. In a comparative experiment, absorbance values of a sample solution were measured and taken for the PLS fit at all those wavenumbers from 1181 to 960 cm$^{-1}$ which have been used for recording the spectra of FIGS. 4 or 5. Then, the root of mean square error of cross-validation (RMSECV) which indicates the standard deviation of the measured values from the standard curve and thus indicates the prediction error for the glucose concentration was 3.44 mg/dl. However, obtaining the entire spectrum of the measured solution in a broad wavelength region caused problems with measurement duration and sample heating.

To overcome these problems, the infrared absorbance is obtained in accordance with the present embodiment at certain distinct wavelengths only. When, other than in the comparative experiment, absorbance by the sample solution is measured only at maxima with wavenumbers of 1151, 1105, 1080, 1036 and 992 cm$^{-1}$ and at a minimum at 1181 cm$^{-1}$, the error (RMSECV) is 38.1 mg/dl. When further minima are selected at 1140, 1094, 1066, 1014 and 960 cm$^{-1}$ and the absorbance measured at these minima is used for the PLS fit together with the absorbance values measured at the maxima and minima mentioned before, the RMSECV value is only 5.28 mg/dl. And the measurement can be completed in a short time without unduly heating the sample. Hence, selecting a sufficient number of minima and maxima for the absorbance measurement can maintain the error at a tolerable value close to the error achievable by using the entire spectrum, but still avoids the disadvantages of using the entire spectrum.

Measuring the absorbance at discrete wavelengths at maxima or minima of absorption bands means in practice to measure the absorbance of an infrared light beam having a bandwidth smaller than the width of the corresponding absorption or transmission band. Preferably, the bandwidth of the light beam should not exceed ⅔ or ⅓ the width of the band of the absorption spectrum where the minimum or maximum is measured.

Hence, the embodiment measures light absorption photoacoustically with laser light at a plurality of discrete individual wavelengths where the largest photoacoustic effect on the glucose concentration is expected. The photoacoustic effect allows measurement of the light absorbance by glucose even where virtually no light escapes again from the body tissue under investigation. And the use of discrete wavelengths allows sufficient laser beam power concentrated to these wavelengths while avoiding unnecessary heating of the body tissue through irradiation with other less favorable wavelengths. The preferred device for emitting the mid-infrared radiation at selected wavelengths, with sufficient intensity but limited overall power so as to avoid overheating of the body tissue is a semiconductor laser having a quantum well structure.

These measures allow noninvasive testing and monitoring of glucose concentrations. Hence, diabetics can conveniently monitor their blood glucose concentrations themselves at short intervals.

The present invention may be embodied in other specific forms without departing from the essential spirit or attributes thereof. The described embodiments should be considered in all respects as illustrative, not restrictive.

What is claimed is:

1. An apparatus for detecting a substance in a sample, comprising:
    a laser device for irradiating the sample with a light beam which penetrates into the sample,
    an acoustic detector for detecting acoustic signals originating within the sample from absorption of the light beam, and
    an indication unit coupled to the acoustic detector for indicating the presence of a substance from the detected acoustic signals,
    wherein the laser device generates infrared light of at least two discrete wavelengths in a mid-infrared wavelength region of 2.5 to 25 μm, each discrete wavelength at a different peak or valley in the absorption spectrum of an substance in the sample, and wherein the indication unit indicates the presence of the substance based on acoustic signals detected for each of said discrete wavelengths.

2. An apparatus according to claim 1, wherein said discrete wavelengths include one at a peak and one at a valley in the absorption spectrum.

3. An apparatus according to claim 1, wherein said discrete wavelengths include at least three distinct wavelengths each at a peak or valley in the absorption spectrum.

4. An apparatus according to claim 1, wherein said laser device emits said at least two discrete wavelengths as individual laser beam pulses at different times to a same location of the sample.

5. An apparatus according to claim 1, wherein the laser device includes a semiconductor laser having a quantum well structure.

6. An apparatus according to claim 5, wherein the semiconductor laser is a quantum cascade laser.

7. An apparatus according to claim 1, wherein said indication unit includes calculating means for calculating the concentration of a substance from-the amplitude of the acoustic signal at each of said discrete wavelengths by a least square method based on a reference spectrum.

8. A method for detecting a substance in a sample, comprising the following steps:
    irradiating the sample with a laser light beam which penetrates into the sample,
    detecting acoustic signals originating within the sample from absorption of the laser light beam, and
    indicating a presence of the substance from the detected acoustic signals,
    wherein said laser light beam is generated at at least two discrete wavelengths in a mid-infrared wavelength region of 2.5 to 25 μm, each discrete wavelength at a different peak or valley in a absorption spectrum of the substance in the sample, and the presence of the substance is indicated based on the acoustic signal detected for each of said discrete wavelengths.

9. An apparatus for detecting a substance in a sample wherein the substance has an absorption spectrum, comprising:
    a laser device for irradiating the sample with a light beam which penetrates into the sample, the laser device generating the light beam at a plurality of discrete bandwidths in a mid-infrared wavelength region of 2.5 to 25 μm, each discrete bandwidth being located at a different peak or valley bandwidth of an absorption spectrum of the substance and having a bandwidth that is smaller than its corresponding peak or valley bandwidth of the absorption spectrum of the substance;

an acoustic detector for detecting acoustic signals originating within the sample from absorption of the light beam, and an indication unit coupled to the acoustic detector for indicating the presence of the substance from the detected acoustic signals, the indication unit indicating the presence of the substance based on acoustic signals detected for each of the discrete bandwidths.

10. The apparatus of claim 9 wherein each discrete bandwidth of the light beam does not exceed two thirds of the width of its corresponding peak or valley bandwidth of the absorption spectrum of the substance.

11. The apparatus of claim 9 wherein each discrete bandwidth of the light beam does not exceed one third of the width of its corresponding peak or valley bandwidth of the absorption spectrum of the substance.

12. The apparatus of claim 9 wherein the discrete bandwidths include at least one bandwidth at each peak or valley bandwidth of the absorption spectrum.

13. The apparatus of claim 9 wherein the laser device includes a semiconductor laser having a quantum well structure.

14. The apparatus of claim 13 wherein the semiconductor laser is a quantum cascade laser.

15. The apparatus of claim 9 wherein the indication unit includes means for calculating a concentration of the substance from the amplitude of the acoustic signal at each discrete bandwidth by a least square method based on a reference spectrum.

16. The apparatus of claim 15 wherein the calculating means discards a portion of each acoustic signal, which in accordance with a traveling time of the signal, originates from a portion of the sample where no useful information on the substance is expected.

17. A method for detecting a substance in a sample wherein the substance has an absorption spectrum, comprising the following steps:

irradiating the sample with a laser light beam which penetrates into the sample, the light beam being at a plurality of discrete bandwidths in a mid-infrared wavelength region of 2.5 to 25 $\mu$m, each discrete bandwidth being located at a different peak or valley bandwidth of the absorption spectrum of the substance and having a bandwidth that is smaller than its corresponding peak or valley bandwidth of the absorption spectrum of the substance:

detecting acoustic signals originating within the sample from absorption of the laser light beam, and indicating a presence of the substance based on the acoustic signals detected for each of the discrete bandwidths.

18. The method of claim 17 wherein each discrete bandwidth of the light beam does not exceed two thirds of the width of its corresponding peak or valley bandwidth of the absorption spectrum of the substance.

19. The method of claim 17 wherein each discrete bandwidth of the light beam does not exceed one third of the width of its corresponding peak or valley bandwidth of the absorption spectrum of the substance.

20. The method of claim 17 wherein the discrete bandwidths include at least one bandwidth at each peak or valley peak or valley bandwidth of the absorption spectrum.

* * * * *